(12) United States Patent
Iio et al.

(10) Patent No.: US 9,114,201 B2
(45) Date of Patent: Aug. 25, 2015

(54) STORAGE CASE FOR PHARMACEUTICAL SYRINGE UNIT

(71) Applicant: Panasonic Healthcare Co., Ltd., Ehime (JP)

(72) Inventors: Toshiaki Iio, Ehime (JP); Yukihiro Takabatake, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 14/356,862

(22) PCT Filed: Oct. 12, 2012

(86) PCT No.: PCT/JP2012/006572
§ 371 (c)(1),
(2) Date: May 7, 2014

(87) PCT Pub. No.: WO2013/069209
PCT Pub. Date: May 16, 2013

(65) Prior Publication Data
US 2014/0360903 A1    Dec. 11, 2014

(30) Foreign Application Priority Data
Nov. 10, 2011   (JP) .................................. 2011-246777

(51) Int. Cl.
*B65D 83/10* (2006.01)
*A61M 5/00* (2006.01)
(Continued)

(52) U.S. Cl.
CPC ............... *A61M 5/002* (2013.01); *A61M 5/008* (2013.01); *A61J 1/16* (2013.01); *A61M 5/20* (2013.01); *A61M 5/2066* (2013.01); *A61M 5/2448* (2013.01); *A61M 2005/206* (2013.01)

(58) Field of Classification Search
USPC .................. 206/363, 364, 470, 471, 564, 570
See application file for complete search history.

(56) References Cited

U.S. PATENT DOCUMENTS 3,013,656 A    12/1961   Murphy
3,910,410 A  * 10/1975   Shaw ......................... 220/359.3
(Continued)

FOREIGN PATENT DOCUMENTS

EP    0525029 A4    3/1993
EP    1066847 A1    1/2001
(Continued)

OTHER PUBLICATIONS

International Search Report for Application No. PCT/JP2012/006572 dated Dec. 25, 2012.
(Continued)

*Primary Examiner* — Jacob K Ackun
(74) *Attorney, Agent, or Firm* — Pearne & Gordon LLP

(57) ABSTRACT

A storage case (100) for storing a pharmaceutical syringe unit (4) that is mounted to a pharmaceutical administering device (8) comprises a base body (1) that is open at its upper face, and a cover (2) for covering the opening in the base body (1). The base body (1) has in its interior a concave portion (5) that holds the cylindrical pharmaceutical syringe unit (4). The concave portion (5) has holders (6) that hold two ends of the pharmaceutical syringe unit (4), and a center concave portion (7) for attaching and removing the pharmaceutical syringe unit (4) and being provided in a position that corresponds to the main body portion of a stored pharmaceutical syringe unit (4). The center concave portion (7) further has a bottom part positioned lower than the holders (6), and is formed such that the pharmaceutical administering device (8) can be disposed in an upright position.

5 Claims, 15 Drawing Sheets

(51) Int. Cl.
*A61M 5/20* (2006.01)
*A61M 5/24* (2006.01)
*A61J 1/16* (2006.01)

(56) References Cited

U.S. PATENT DOCUMENTS

| | | | |
|---|---|---|---|
| 4,420,085 A | 12/1983 | Wilson et al. | |
| 4,782,949 A * | 11/1988 | Berkman | 206/387.14 |
| 5,031,768 A | 7/1991 | Fischer | |
| 5,082,112 A * | 1/1992 | Dunklee | 206/363 |
| 5,209,352 A * | 5/1993 | Light et al. | 206/391 |
| 5,626,226 A * | 5/1997 | Gardiner et al. | 206/349 |
| 5,890,593 A * | 4/1999 | Humphrey | 206/471 |
| 5,947,291 A * | 9/1999 | Humphrey | 206/463 |
| 6,000,548 A | 12/1999 | Tsals | |
| 6,003,671 A * | 12/1999 | McDonough et al. | 206/493 |
| 6,228,324 B1 * | 5/2001 | Hasegawa et al. | 422/30 |
| 6,645,179 B1 | 11/2003 | Ishikawa et al. | |
| 7,093,595 B2 * | 8/2006 | Nesbitt | 128/203.15 |
| 8,042,689 B2 * | 10/2011 | Frojd et al. | 206/464 |
| 8,104,615 B2 * | 1/2012 | Liu | 206/373 |
| 8,303,599 B2 | 11/2012 | Hess et al. | |
| 8,398,602 B2 | 3/2013 | Ilo et al. | |
| 8,403,936 B2 | 3/2013 | Hess et al. | |
| 8,674,656 B2 | 3/2014 | Iio et al. | |
| 8,945,134 B2 | 2/2015 | Hess et al. | |
| 2007/0185495 A1 | 8/2007 | Hess et al. | |
| 2007/0225654 A1 | 9/2007 | Hess et al. | |
| 2009/0194446 A1 | 8/2009 | Miller et al. | |
| 2011/0015640 A1 | 1/2011 | Hess et al. | |
| 2011/0192751 A1 * | 8/2011 | Doster | 206/459.5 |
| 2011/0218502 A1 | 9/2011 | Iio et al. | |
| 2013/0175192 A1 | 7/2013 | Iio et al. | |
| 2013/0186511 A1 | 7/2013 | Hess et al. | |

FOREIGN PATENT DOCUMENTS

| | | |
|---|---|---|
| EP | 0988072 B1 | 3/2004 |
| EP | 1066847 B1 | 6/2004 |
| EP | 1813299 A2 | 8/2007 |
| EP | 2357013 A1 | 8/2011 |
| JP | H05-509059 A | 12/1993 |
| JP | 2001-017545 A | 1/2001 |
| JP | 2002-507952 A | 3/2002 |
| JP | 2006-326192 A | 12/2006 |
| JP | 2007-216009 A | 8/2007 |
| WO | 91/15411 A1 | 10/1991 |
| WO | 98/57681 A1 | 12/1998 |
| WO | 00/51667 A1 | 9/2000 |
| WO | 2010/055608 A1 | 5/2010 |

OTHER PUBLICATIONS

Extended European Search Report for Application No. 12847356.8-1662/2777683 PCT/JP2012006572 dated Mar. 13, 2015.
Notice of Allowance for Application No. JP 2013-542813 dated Jun. 23, 2015.

\* cited by examiner

STORAGE CASE FOR PHARMACEUTICAL SYRINGE UNIT

TECHNICAL FIELD

The present invention relates to a storage case for storing a pharmaceutical syringe unit that is used for administering a growth hormone, for example.

BACKGROUND ART

For instance, a pharmaceutical syringe unit that is used for administering a growth hormone is mounted to a pharmaceutical administering device, and administration is performed one or more times a day (see the following Patent Literature 1, for example). When the administration is finished, the pharmaceutical syringe unit is removed from the pharmaceutical administering device, placed in a storage case, and stored in a refrigerator or the like.

CITATION LIST

Patent Literature

Patent Literature 1: Japanese Laid-Open Patent Application 2001-17545

SUMMARY

Technical Problem

The above-mentioned storage case has a base body that is open at its upper face, and a cover for covering the opening in the base body. The pharmaceutical syringe unit is put inside the base body, covered with the cover, and then stored in a refrigerator or the like. When it is time to administer the pharmaceutical, the pharmaceutical syringe unit is taken out of the storage case and mounted to the pharmaceutical administering device as discussed above. That is, the storage case is necessary for storing a pharmaceutical syringe unit, but it serves no purpose at all during pharmaceutical administration, and in fact can get in the way.

In view of this, it is an object of the present invention to provide a storage case for a pharmaceutical syringe unit that can be effectively used even during pharmaceutical administration.

SOLUTION TO PROBLEM

To achieve the stated object, in one aspect of the present invention, a storage case for storing a cylindrical pharmaceutical syringe unit that is mounted to a pharmaceutical administering device comprises a base body having an opening at an upper face of the base body, and a cover configured to cover the opening of the base body. The base body includes in an interior thereof a concave portion configured to hold the cylindrical pharmaceutical syringe unit. The concave portion includes holders configured to hold two ends of the cylindrical pharmaceutical syringe unit respectively, and a center concave portion provided in a position that corresponds to a main body portion of the cylindrical pharmaceutical syringe unit when the cylindrical pharmaceutical syringe unit is held, the center concave portion being configured to be used for attaching and removing the cylindrical pharmaceutical syringe unit. The center concave portion has a bottom part disposed lower than the holders, and is formed such that the pharmaceutical administering device can be disposed in an upright position.

ADVANTAGEOUS EFFECTS

As discussed above, the present invention provides a storage case for a pharmaceutical syringe unit that can be used effectively even during pharmaceutical administration.

DESCRIPTION OF EMBODIMENTS

An embodiment of the present invention will now be described through reference to the appended drawings.
Embodiment 1

Figure 1:
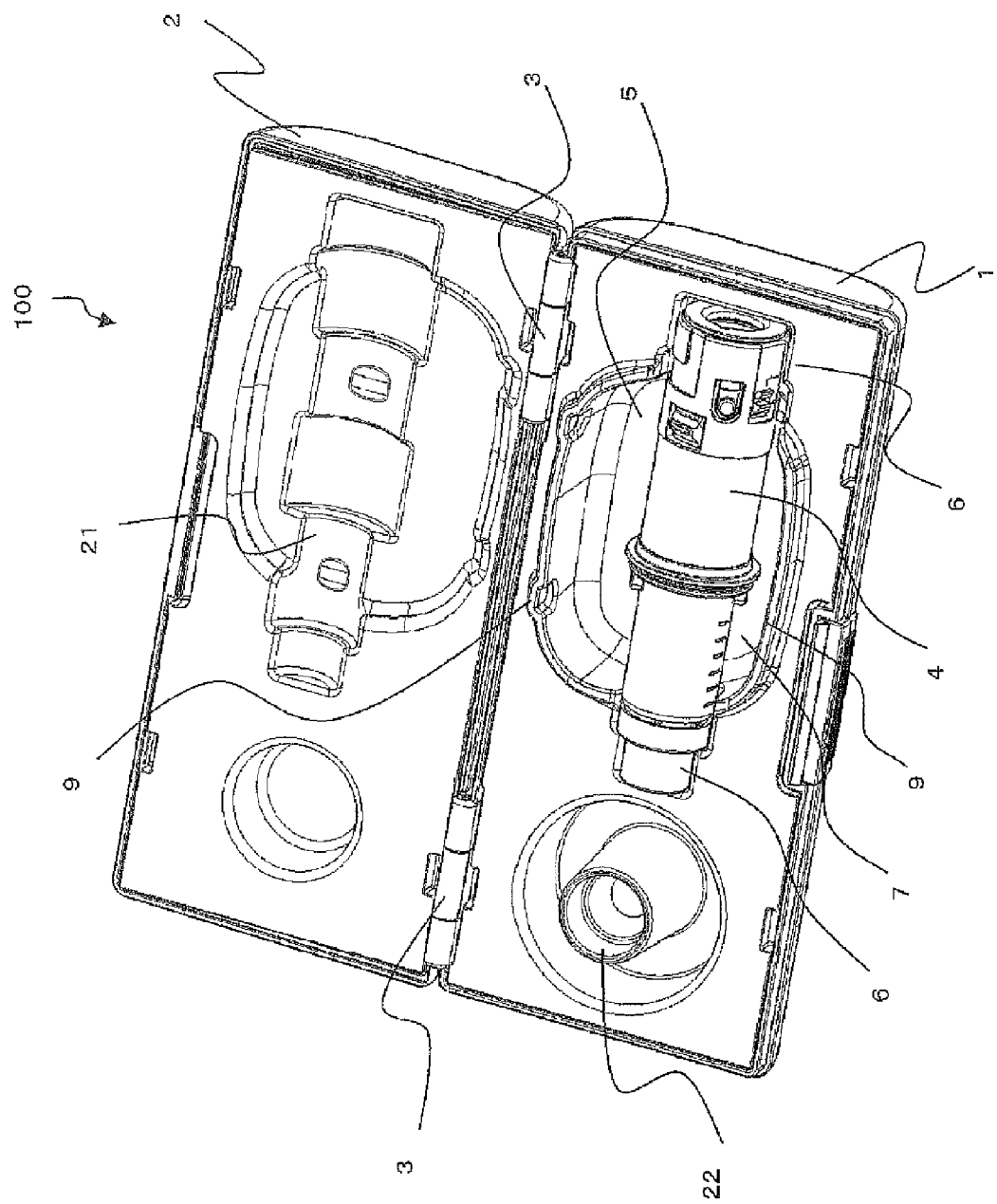
FIG. 1 is an oblique view of the storage case for a pharmaceutical syringe unit pertaining to an embodiment of the present invention.
Figure 2:
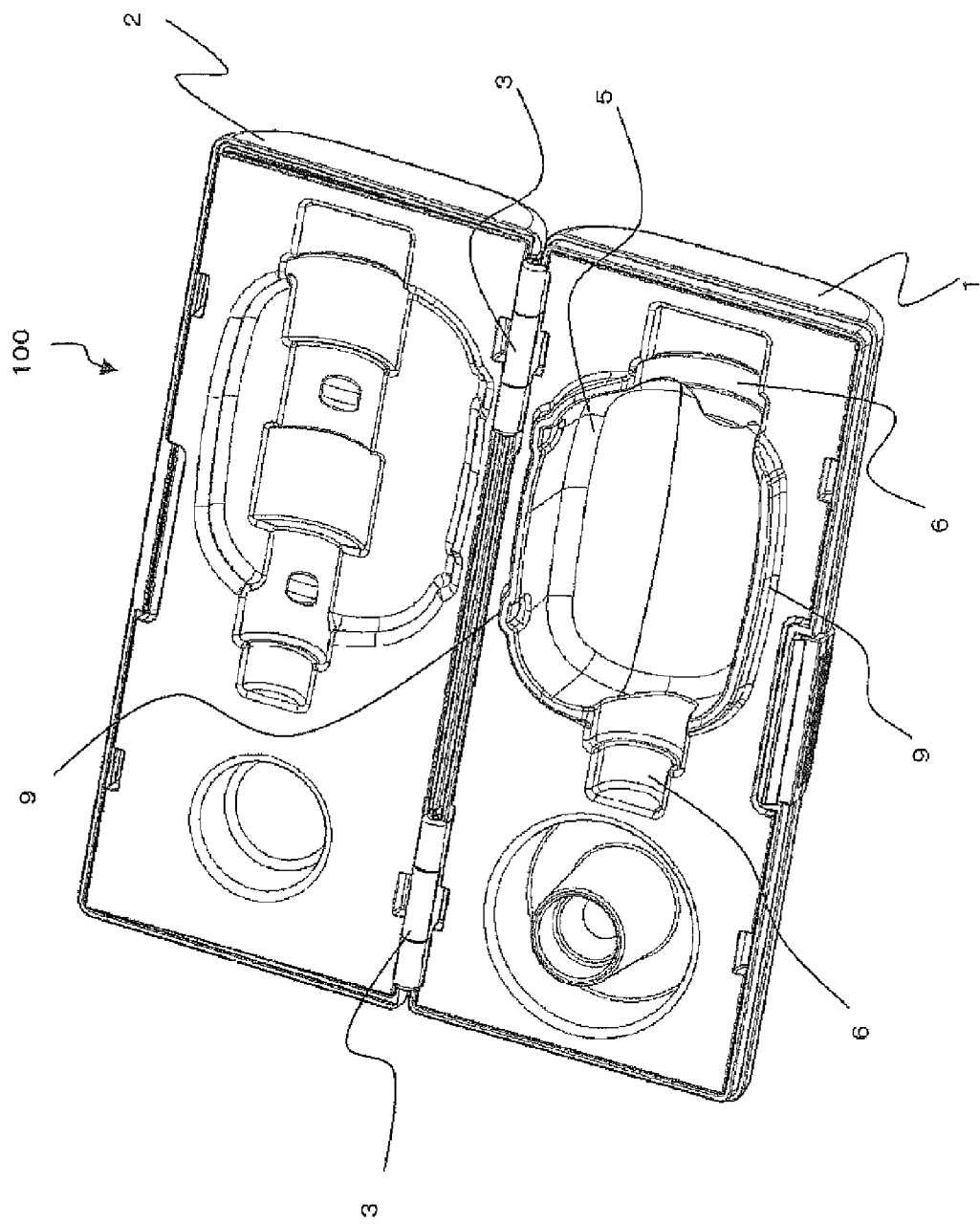
FIG. 2 is an oblique view of the same.
Figure 3:
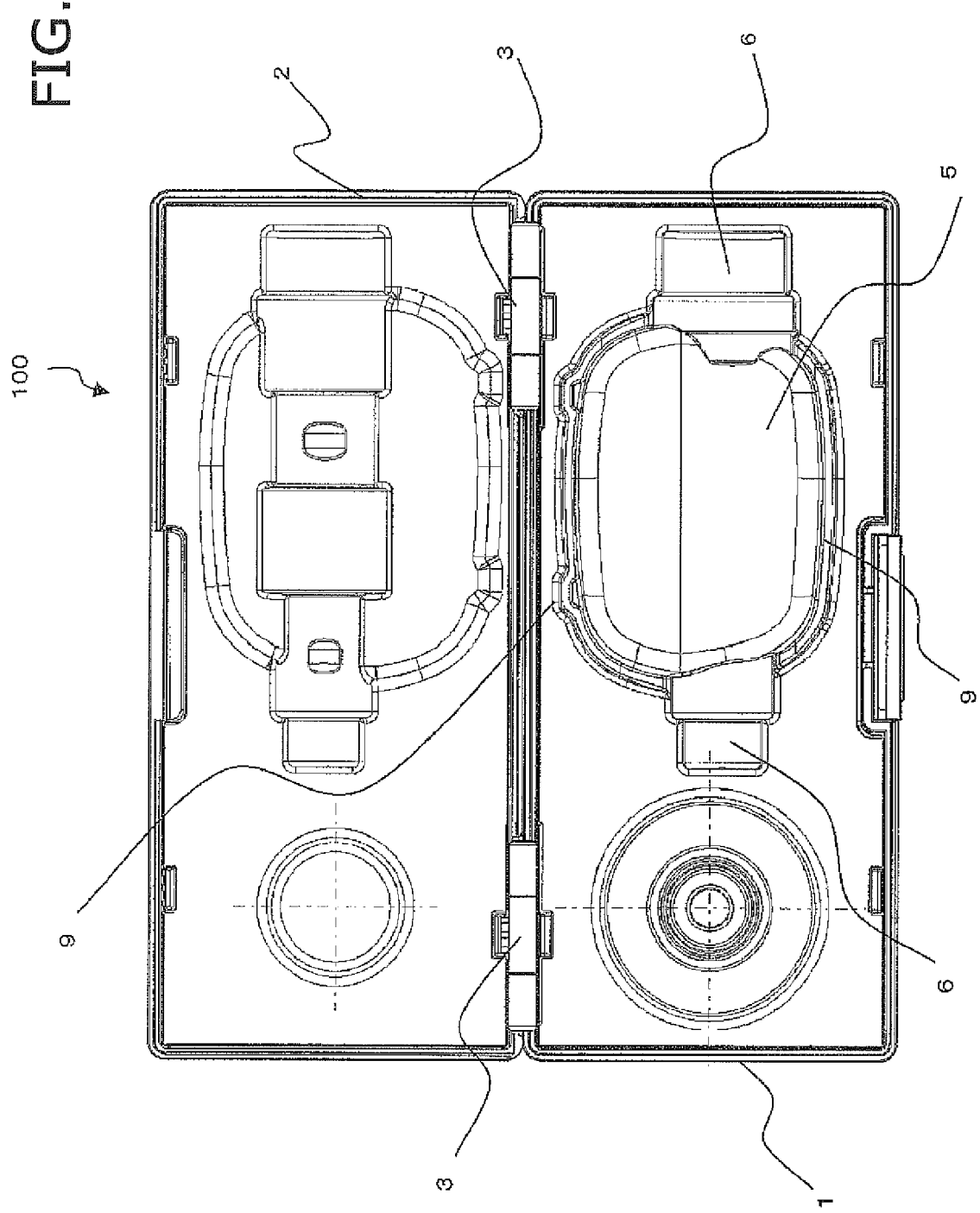
FIG. 3 is a plan view of the same.

As shown in FIGS. 1 to 3, the storage case 100 in this embodiment is a storage case for storing a pharmaceutical syringe unit 4 that is mounted to a pharmaceutical administering device, and is made up of a rectangular base body 1 that is open at its upper face, and a cover 2 that covers the upper face (an example of a first face) of this base body 1. More specifically, one long side of the base body 1 and one long side of the cover 2 are linked by a hinge 3, and the cover 2 opens and closes with respect to the upper face of the base body 1 using this hinge 3 as its axis.

Figure 4:
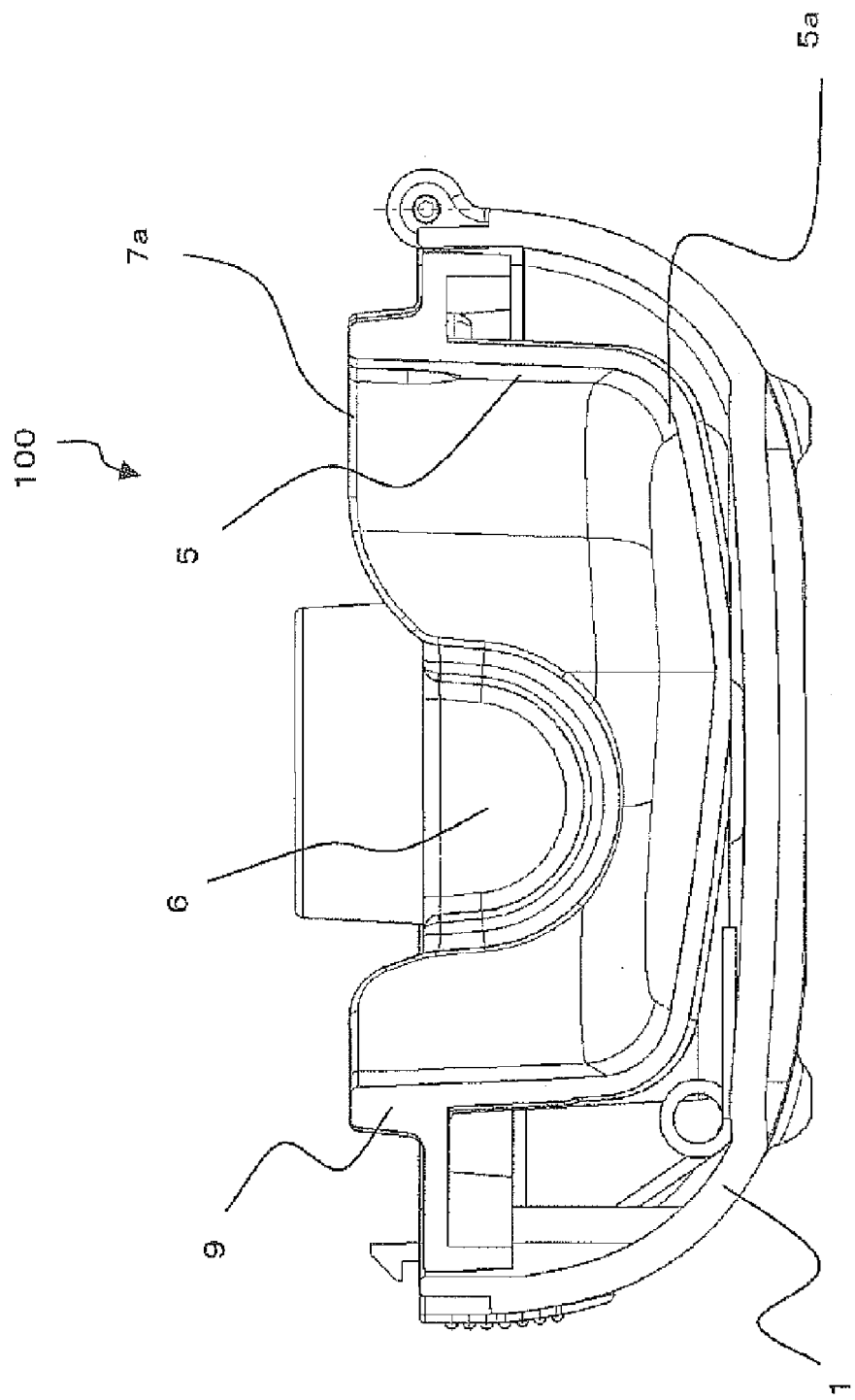
FIG. 4 is a cross sectional view of the same.
Figure 6:
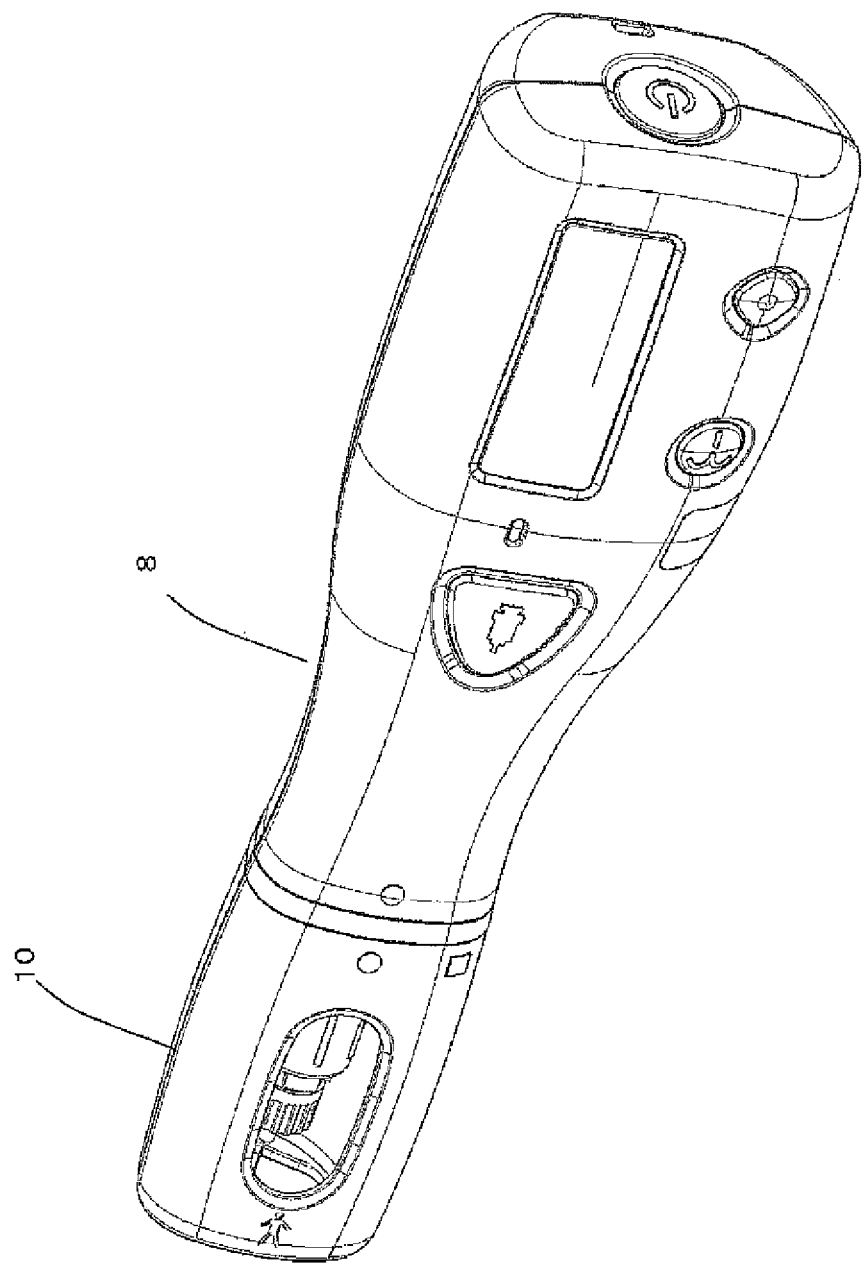
FIG. 6 is an oblique view showing an appearance of the pharmaceutical administering device.

The base body 1 has in its interior a concave portion 5 that holds the pharmaceutical syringe unit 4 having a cylindrical shape. This concave portion 5 has holders 6 (an example of first concave portions) that hold two ends of the pharmaceutical syringe unit 4 respectively, and a center concave portion 7 (an example of a second concave portion) disposed between the holders 6. The center concave portion 7 is provided in a position that corresponds to a main body portion of the stored pharmaceutical syringe unit 4, such as an outer peripheral part of a middle body of the pharmaceutical syringe unit 4. The center concave portion 7 has an opening 7a (FIG. 4) that is larger than openings of the holders 6, and the opening 7a is used when the pharmaceutical syringe unit 4 is removed from or placed in the storage case, as will be discussed below. As shown in FIG. 4, the center concave portion 7 has a bottom part 5a disposed lower than the holders 6, and is formed so that the pharmaceutical administering device 8 can be disposed in an upright position by holding the rear end of the pharmaceutical administering device 8 (FIG. 6; discussed below). That is, the concave portion 5 serves both to hold the pharmaceutical syringe unit 4 and to hold the pharmaceutical administering device 8 upright. After the pharmaceutical syringe unit 4 shown in FIG. 1 has been taken out of the concave portion 5, the pharmaceutical administering device 8 can be installed in an upright position in the concave portion 5.

To stabilize the upright position of the pharmaceutical administering device 8, the center concave portion 7 is provided with a retainer wall 9 that protrudes upward from all the way around the outer peripheral part surrounding the opening 7a.

With the above configuration, as shown in FIG. 1, the pharmaceutical syringe unit 4 is placed inside the concave portion 5 of the base body 1. The storage case 100 is stored in this state in a refrigerator or the like, with the cover 2 closed over the upper face opening. At the time of use, as shown in FIG. 1, the cover 2 is opened to expose the pharmaceutical syringe unit 4. In this state, fingers of a user are inserted into the concave portion 5 through the opening 7a, which is used for removing the pharmaceutical syringe unit and is located on both sides of the main body portion of the pharmaceutical syringe unit 4, and the pharmaceutical syringe unit 4 is lifted out of the concave portion 5 with the fingers. The pharmaceutical syringe unit 4 is then mounted to the pharmaceutical administering device 8.

Figure 5:
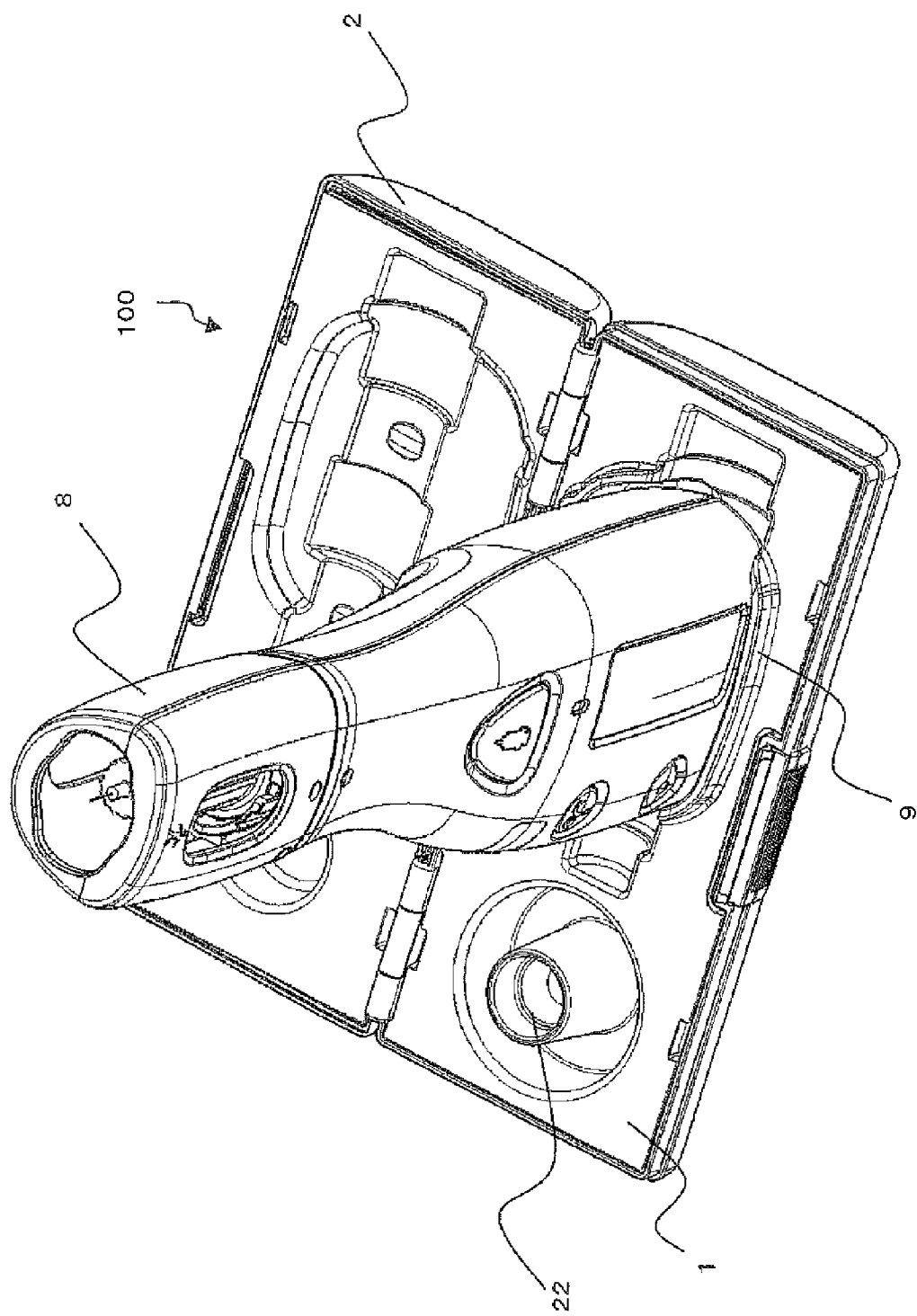
FIG. 5 is an oblique view of a pharmaceutical administering device that is installed in an upright position in the storage case.

Thus, when the pharmaceutical syringe unit 4 is mounted to the pharmaceutical administering device 8 and not stowed in the storage case 100, the concave portion 5 of the base body 1 in the storage case 100 is left open as shown in FIG. 2. The rear end of the pharmaceutical administering device 8 is then inserted into the center concave portion 7 of the concave portion 5, and the pharmaceutical administering device 8 is disposed in an upright position as shown in FIG. 5. That is, in this embodiment, the center concave portion 7 of the concave portion 5 has substantially the same shape as the rear end of the pharmaceutical administering device 8, and its opening diameter is slightly larger than the rear end of the pharmaceutical administering device 8. Therefore, as discussed above, the rear end of the pharmaceutical administering device 8 can be inserted into the center concave portion 7, and the pharmaceutical administering device 8 can be disposed in an upright position as shown in FIG. 5.

Figure 7:
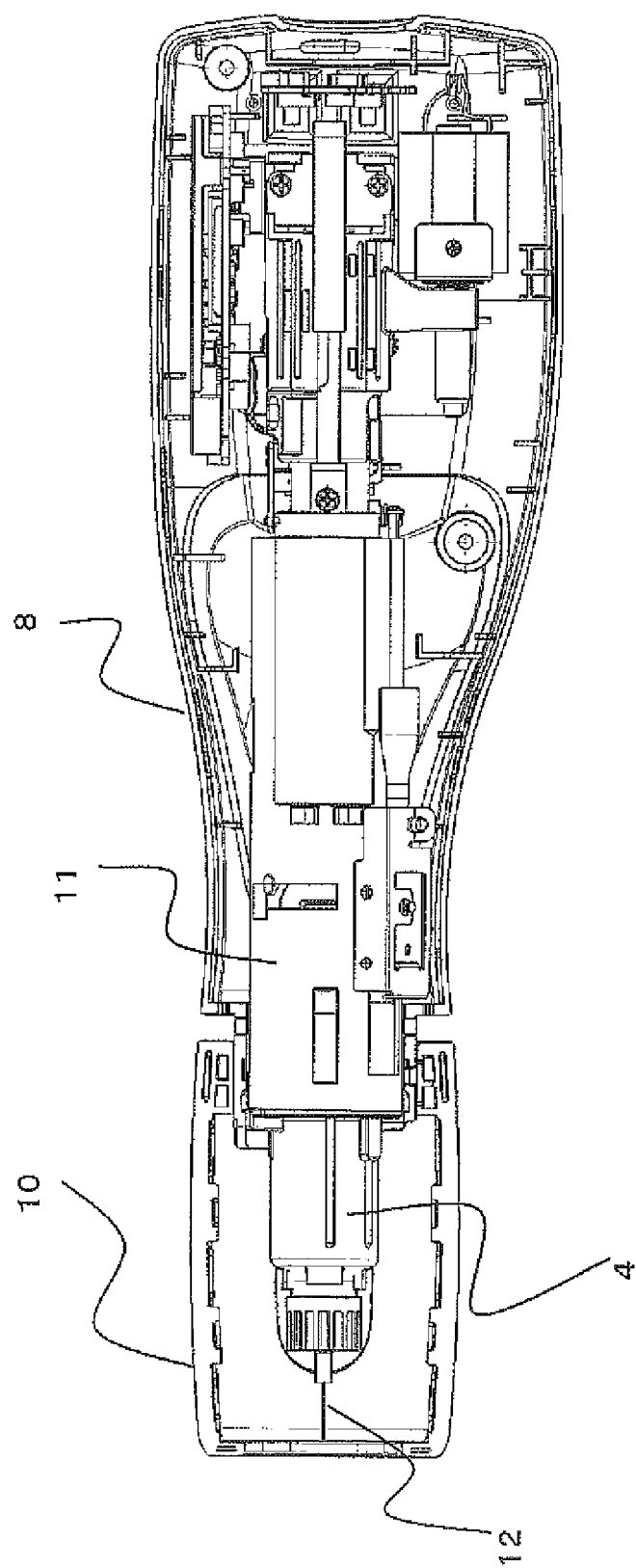
FIG. 7 is a cross sectional view of this pharmaceutical administering device.
Figure 8:
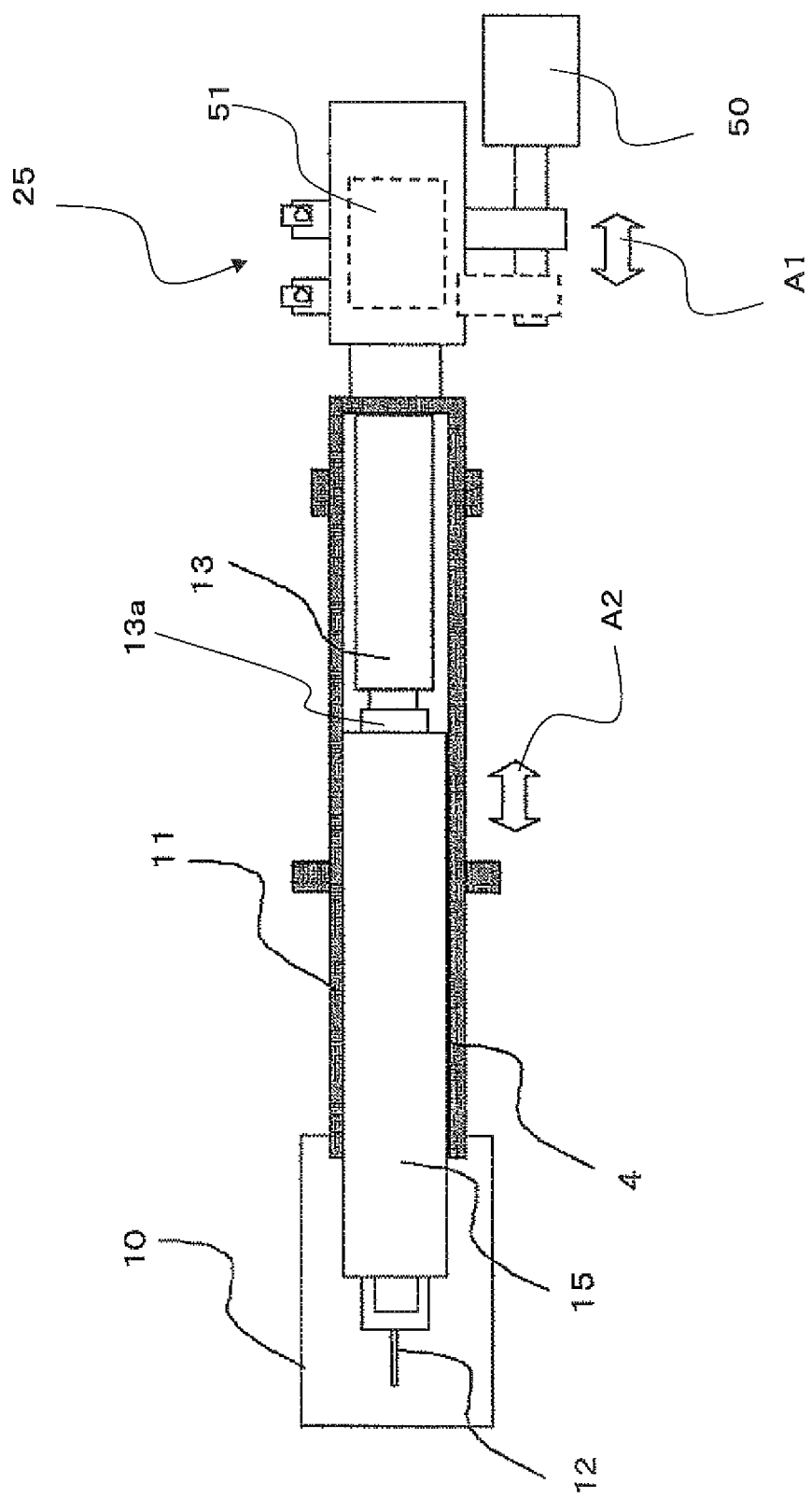
FIG. 8 is a diagram of a main part of the pharmaceutical administering device.

FIGS. 6 and 7 show an example of the pharmaceutical administering device 8. As shown in FIG. 6, the pharmaceutical administering device 8 has an overall rectangular shape, and a distal end cap 10 is provided to the distal end thereof. An inner case 11 is provided as shown in FIG. 7 in the interior of pharmaceutical administering device 8. As shown in FIG. 8, the pharmaceutical syringe unit 4 is mounted inside this inner case 11. An injection needle 12 is mounted to the distal end of the pharmaceutical syringe unit 4. In this state, a piston driver 25 is driven in the arrow A1 direction by a slide motor 50, which causes the inner case 11 including a piston unit 13 to move in the arrow A2 direction. This drive of the slide motor 50 causes the inner case 11 to slide, and performs needle insertion and retraction in which the injection needle 12 comes out of or is pulled back into the distal end cap 10. Meanwhile, the drive of a piston motor 51 allows a piston 13a incorporated into the piston unit 13 to slide, and when it is moved to the left in FIG. 8, the pharmaceutical syringe unit 4 performs the mixing and dissolution of solid and liquid pharmaceuticals, air venting, and pharmaceutical administration.

Figure 9A:
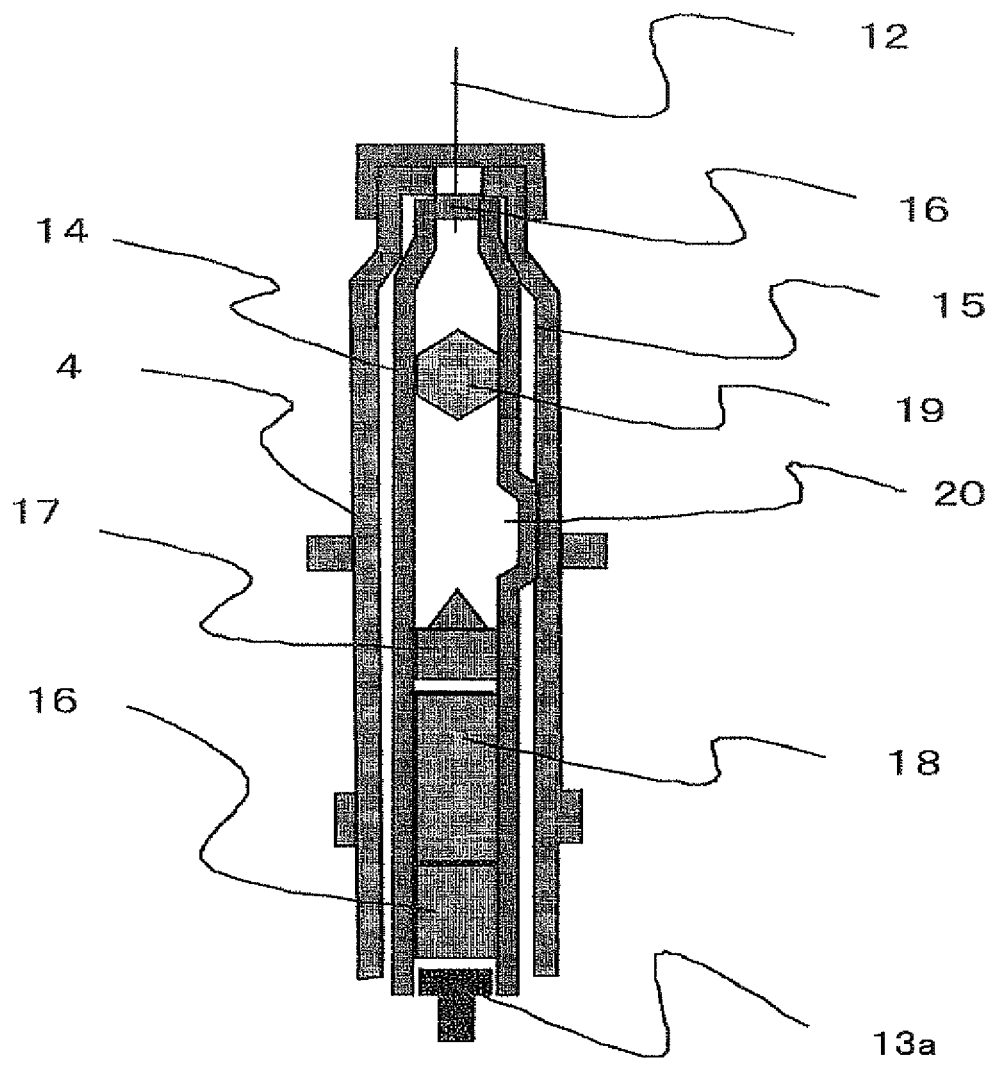
FIG. 9A is a diagram illustrating the operation of the pharmaceutical administering device.
Figure 9B:
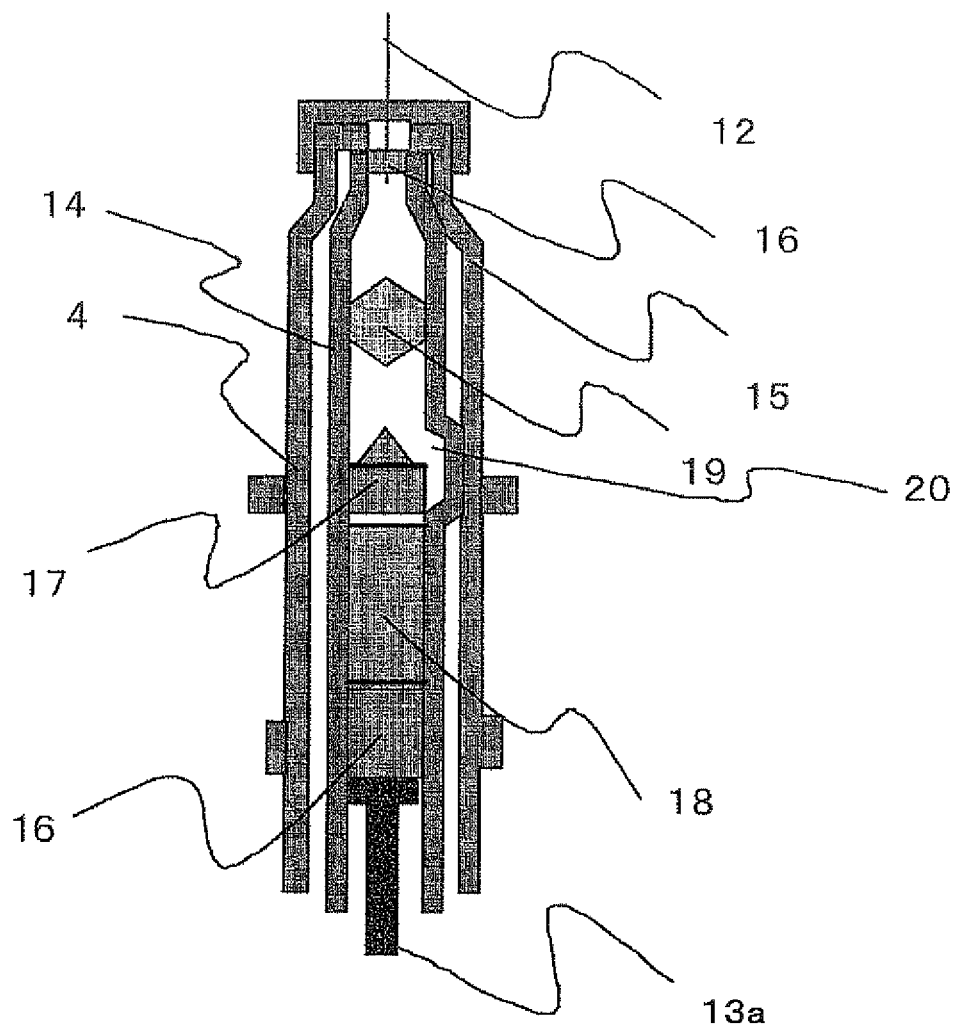
FIG. 9B is a diagram illustrating the operation of the pharmaceutical administering device.
Figure 9C:
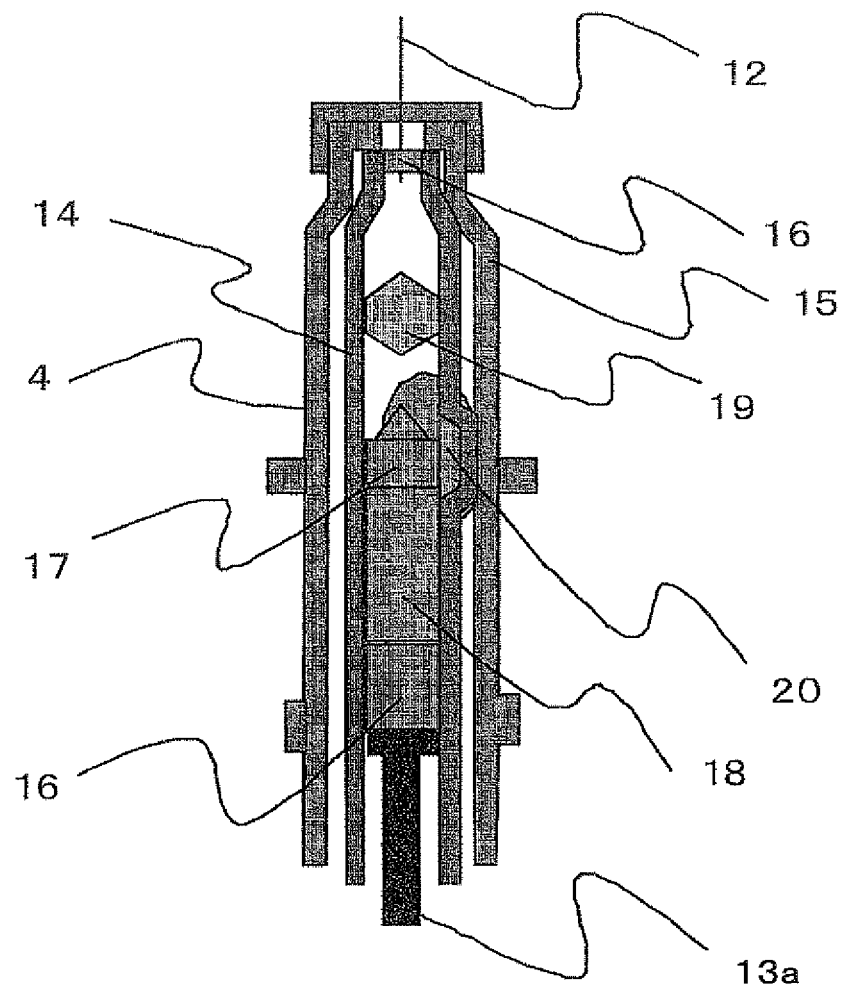
FIG. 9C is a diagram illustrating the operation of the pharmaceutical administering device.
Figure 9D:
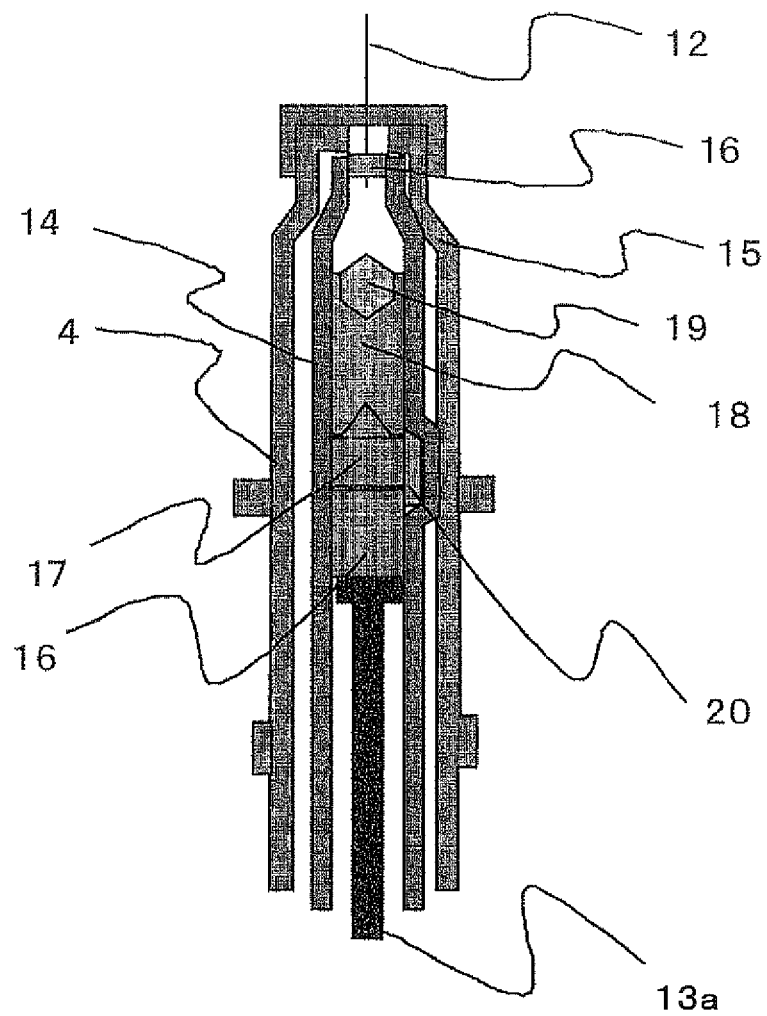
FIG. 9D is a diagram illustrating the operation of the pharmaceutical administering device.

The operation of the pharmaceutical administering device 8 under the drive of the piston 13a incorporated into the piston unit 13 will now be described in specific terms through reference to FIGS. 9A to 9F. FIG. 9A shows the pharmaceutical syringe unit 4. This pharmaceutical syringe unit 4 is made up of a cylindrical pharmaceutical syringe 14 and a cylindrical cover 15 provided around the outside thereof. Gaskets 16 and 17 are provided on the rear end side and in the middle of the pharmaceutical syringe 14, and a liquid pharmaceutical 18 is housed between these gaskets 16 and 17. In addition, a solid pharmaceutical 19 is housed between the middle and the distal end of the pharmaceutical syringe 14. In this state, as shown in FIGS. 9A, 9B, and 9C, the gasket 16 is pushed toward the distal end side by the piston 13a incorporated into the piston unit 13. As shown in FIG. 9C, at the point when the gasket 17 reaches a bypass 20 provided in the middle of the pharmaceutical syringe 14, the liquid pharmaceutical 18 goes through this bypass 20 and begins to be mixed with the solid pharmaceutical 19. After a while, the state shown in FIGS. 9D and 9E results, and the liquid pharmaceutical 18 and the solid pharmaceutical 19 are mixed and dissolved.

As shown in FIG. 5, this mixing and dissolution of the liquid pharmaceutical 18 and the solid pharmaceutical 19 can be performed in a state in which the pharmaceutical administering device 8 has been disposed in an upright position in the concave portion 5 of the base body 1 of the storage case 100. Thus, the configuration in this embodiment, in which the base body 1 of the storage case 100 can hold the pharmaceutical administering device 8 in an upright position, makes the device extremely convenient to use.

Figure 9E:
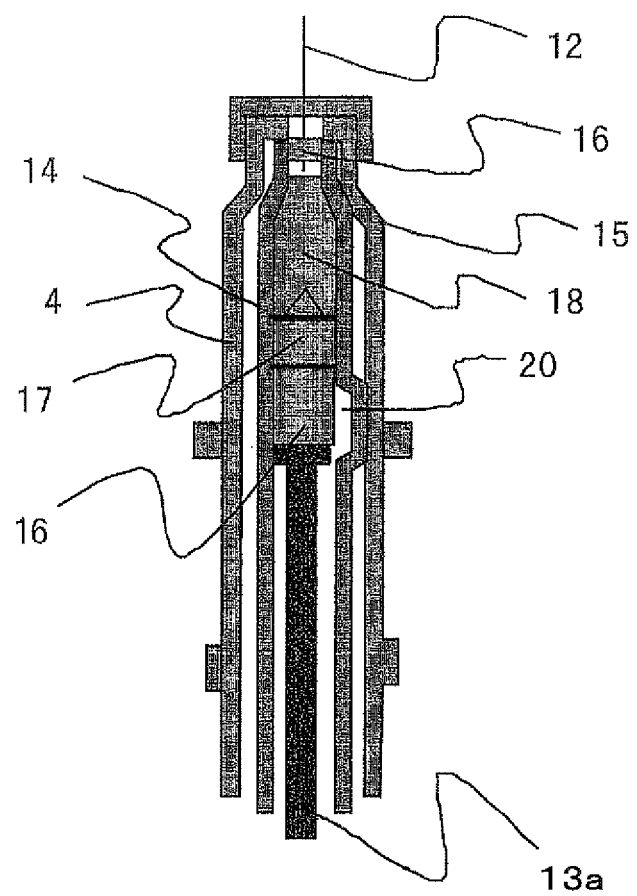
FIG. 9E is a diagram illustrating the operation of the pharmaceutical administering device.
Figure 9F:
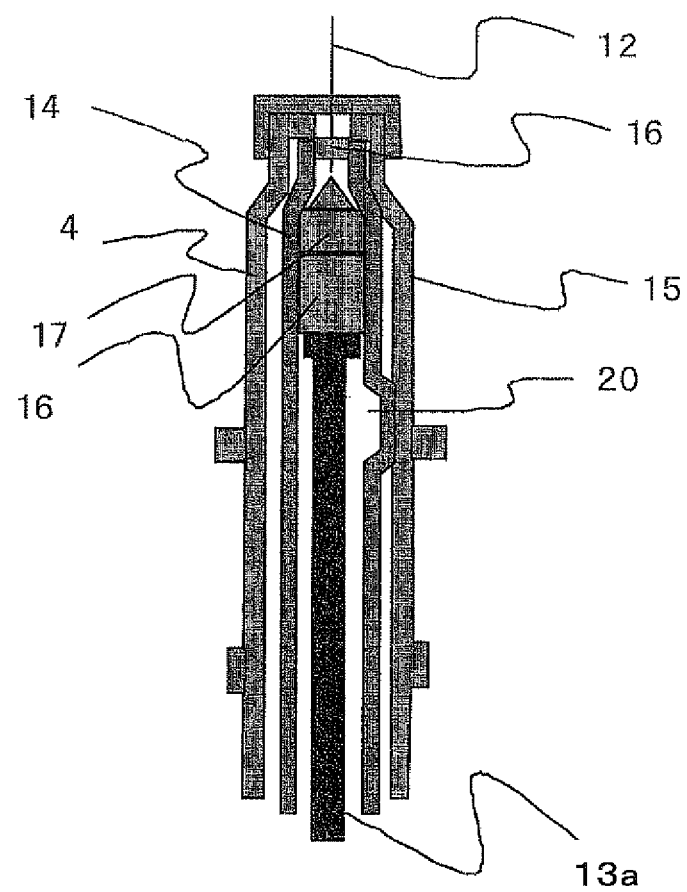
FIG. 9F is a diagram illustrating the operation of the pharmaceutical administering device.

After the state in FIG. 9E, the pharmaceutical administering device 8 must vent the air. This is also performed in a state in which the pharmaceutical administering device 8 is held in an upright position in the concave portion 5 of the base body 1, as shown in FIG. 5. If the air venting is performed with the pharmaceutical administering device 8 not in an upright position, then some of the pharmaceuticals will also be discharged along with the air from the injection needle 12, and end up being wasted. Thus, being able to hold the pharmaceutical administering device 8 in an upright position as shown in FIG. 5 makes the device much more convenient to use.

After this, the pharmaceutical administering device 8 is taken out of the concave portion 5 of the base body 1 of the storage case 100, and in this state, the inner case 11 including the piston unit 13 and the injection needle 12 is moved to the distal end side so that the needle is inserted and the pharmaceutical administered.

As shown in FIG. 1, a concave portion 21 is provided to the cover 2 of the storage case 100 to line up with the upper face of the pharmaceutical syringe unit 4. A concave portion 22 for the temporary placement of a protective cap (not shown) of the injection needle 12 is provided next to the concave portion 5 of the base body 1.

As discussed above, the storage case 100 for a pharmaceutical syringe unit pertaining to the above embodiment comprises the base body 1 that is open at its upper face, and the cover 2 that covers the opening in the base body 1. The base body 1 has the concave portion 5, which holds the cylindrical pharmaceutical syringe unit 4 in its interior. The concave portion 5 has the holders 6, which hold two ends of the pharmaceutical syringe unit 4 respectively, and the center concave portion 7, which is provided at a position corresponding to the main body portion of the stored pharmaceutical syringe unit 4 and which is used for attaching and removing the pharmaceutical syringe unit 4. The center concave portion 7 has the bottom part 5a, which is disposed lower than the holders 6, and is formed such that the pharmaceutical administering device can be disposed in an upright position. This allows the storage case 100 to be put to use even during pharmaceutical administration.

Specifically, in this embodiment, the base body 1 of the storage case 100 has in its interior the concave portion 5, which holds the cylindrical pharmaceutical syringe unit 4, and the concave portion 5 has the holders 6, which hold two ends of the pharmaceutical syringe unit 4 respectively, and the center concave portion 7, which is provided at a position corresponding to the main body portion of the stored pharmaceutical syringe unit 4 and which is used for attaching and removing the pharmaceutical syringe unit 4. The bottom part 5a of the center concave portion 7 is disposed lower than the holders 6, and is formed so that the pharmaceutical administering device can be disposed in an upright position.

Therefore, after the pharmaceutical syringe unit 4 is taken out of the concave portion 5 of the base body 1 of the storage case 100, the pharmaceutical administering device 8 can be put in an upright position in the concave portion 5. This allows the storage case 100 to be put to use even during pharmaceutical administration. To describe this point in more specific terms, during pharmaceutical administration, the pharmaceutical administering device 8 is set up perpendicular to the horizontal plane, and in this state, air venting, or the mixing and dissolution of the liquid and solid pharmaceuticals, need be done, for example. Since the pharmaceutical administering device 8 can be held in an upright position in the concave portion 5 of the storage case 100 at this time, these operations can be carried out more smoothly. Therefore, the storage case 100 pertaining to this embodiment can be used not only as a storage case for storing the pharmaceutical syringe unit 4 containing a growth hormone, for example, but also as a means for putting the pharmaceutical administering device 8 in an upright position.

Embodiment 2

Figure 10:
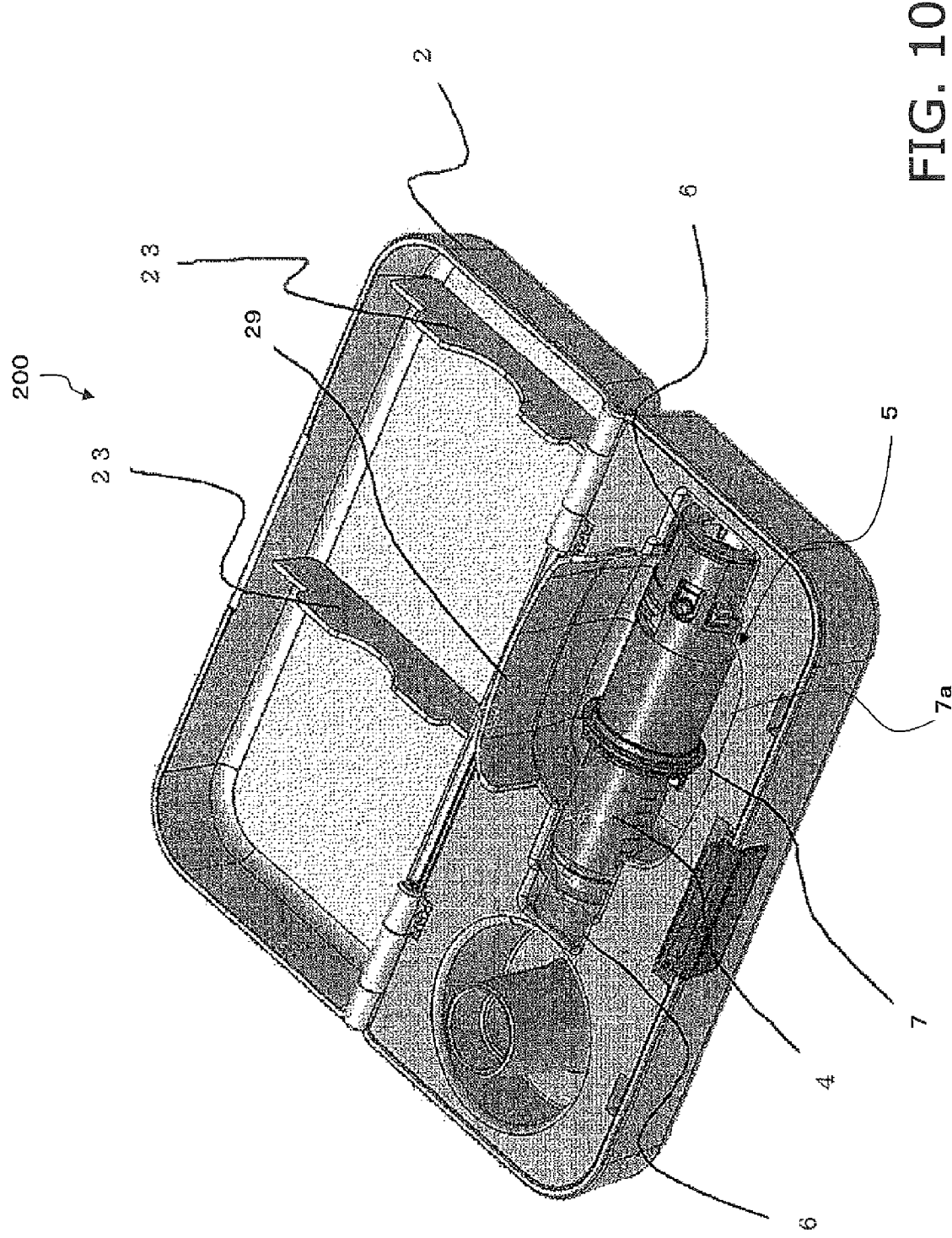
FIG. 10 is an oblique view of the storage case for a pharmaceutical syringe unit pertaining to another embodiment of the present invention.

FIG. 10 shows a storage case 200 for a pharmaceutical syringe unit pertaining to another embodiment. In this embodiment, the cover 2 is provided with a rib 23 that holds down the upper face of the pharmaceutical syringe unit 4. Also, with the storage case 200 pertaining to this embodiment, the center concave portion 7 in the concave portion 5 is provided with a retainer wall 29 that protrudes upward only at a portion of the outer peripheral part of the center concave portion 7. The rest of the components are the same as that in Embodiment 1 above, and are numbered the same and will not be described again.

Other Embodiments

In the above embodiments, the concave portion 5 of the storage cases 100 and 200 has such a configuration that the pharmaceutical syringe unit 4 is held in the holders 6, and the pharmaceutical administering device 8 can be held in an upright position in the center concave portion 7, but this is not the only option. The storage case may instead be such that the portion that holds the pharmaceutical syringe unit 4 and the portion that holds the pharmaceutical administering device 8 in an upright position are formed separately, or such that the portion that holds the pharmaceutical syringe unit 4 and the portion that holds the pharmaceutical administering device 8 in an upright position are formed as portions that share a part with each other.

Industrial Applicability

The storage case for a pharmaceutical syringe unit pertaining to the present invention is used as a storage case, etc., for storing a pharmaceutical syringe unit that is used in administering a growth hormone or other such pharmaceutical, for example.

REFERENCE SIGNS LIST 1 base body
2 cover
3 hinge
4 pharmaceutical syringe unit
5 concave portion
6 holder
7 center concave portion
7a opening
8 pharmaceutical administering device
9 retainer wall
10 distal end cap
11 inner case
12 injection needle
13 piston unit
13a piston
14 pharmaceutical syringe
15 cover
16, 17 gasket
18 liquid pharmaceutical
19 solid pharmaceutical
20 bypass
21, 22 concave portion
23 rib
29 retainer wall

The invention claimed is:

1. A storage case for storing a pharmaceutical syringe unit that is mounted to a pharmaceutical administering device, said storage case comprising:
   a base body including an opening at an upper face of the base body; and
   a cover configured to cover the opening of the base body,
   wherein the base body includes in an interior thereof a concave portion configured to hold the cylindrical pharmaceutical syringe unit,
   the concave portion includes holders configured to hold two ends of the pharmaceutical syringe unit respectively, and a center concave portion provided in a position that corresponds to a main body portion of the cylindrical pharmaceutical syringe unit when the cylindrical pharmaceutical syringe unit is held, the center concave portion being configured to be used for attaching and removing the pharmaceutical syringe unit,
   the center concave portion has a bottom part disposed lower than the holders, and is formed such that the pharmaceutical administering device can be disposed in an upright position, and
   the center concave portion further includes, at an outer peripheral part thereof, a retainer wall that sticks up above the base body.

2. The storage case according to claim 1,
   wherein the retainer wall is formed at a part of the outer peripheral part of the center concave portion.

3. The storage case according to claim 1,
   wherein the center concave portion is disposed between the holders and has an opening that is larger than each opening of the holders.

4. A storage case for storing a pharmaceutical syringe unit that is mounted to a pharmaceutical administering device, said storage case comprising:
- a base body including two first concave portions and a second concave portion disposed between the two first concave portions, the two first concave portions and the second concave portion being open at a first face of the base body; and
- a cover attached to the first face of the base body so as to be capable of opening and closing the first face of the base body,
- wherein the two first concave portions are formed so as to support two ends of the cylindrical pharmaceutical syringe unit when the pharmaceutical syringe unit is stored in the storage case,
- the second concave portion is formed so as to communicate with the two first concave portions and be deeper than the two first concave portions, the second concave portion having an opening at the first face that is larger than each opening of the two first concave portions,
- the second concave portion is formed so as to hold a part of the pharmaceutical administering device so that the pharmaceutical administering device is supported in an upright position, and
- the second concave portion includes, at an outer peripheral part thereof, a retainer wall that sticks up above the first face of the base body.

5. The storage case according to claim 4,
- wherein the retainer wall is formed at a part of the outer peripheral part of the second concave portion.

* * * * *